United States Patent
Schrauzer

(10) Patent No.: US 7,521,065 B2
(45) Date of Patent: Apr. 21, 2009

(54) COMPOSITIONS FOR THE TREATMENT AND PREVENTION OF CANCER

(76) Inventor: Gerhard N. Schrauzer, 175 Alameda Blvd., Coronado, CA (US) 92118

( * ) Notice: Subject to any disclaimer, the term of this patent is extended or adjusted under 35 U.S.C. 154(b) by 239 days.

(21) Appl. No.: 11/007,135

(22) Filed: Dec. 7, 2004

(65) Prior Publication Data

US 2005/0106228 A1 May 19, 2005

Related U.S. Application Data

(62) Division of application No. 10/179,712, filed on Jun. 24, 2002, now Pat. No. 6,867,238.

(60) Provisional application No. 60/300,408, filed on Jun. 22, 2001.

(51) Int. Cl.
*A61K 31/095* (2006.01)
*A61K 9/70* (2006.01)
*A61P 35/00* (2006.01)

(52) U.S. Cl. ...................... 424/449; 514/706

(58) Field of Classification Search ................ 514/706, 514/858–865, 887; 424/449
See application file for complete search history.

(56) References Cited

U.S. PATENT DOCUMENTS

| | | | |
|---|---|---|---|
| 4,512,977 A | 4/1985 | Lundy | |
| 4,865,840 A | 9/1989 | Burke et al. | |
| 5,008,287 A * | 4/1991 | Monti | 514/492 |
| 6,319,911 B1 * | 11/2001 | Rodriguez | 514/170 |
| 2001/0044431 A1 * | 11/2001 | Rodriguez | 514/179 |

FOREIGN PATENT DOCUMENTS

DE 3408362 C2 3/1983
DE 4320694 A1 1/1995

OTHER PUBLICATIONS

Lu, J. et al., "Dissociation of the genotoxic and growth inhibitory effects of selenium," Biochemical Pharmacology, vol. 50 (2), pp. 213-219 (1995).*
Easaki, N. et al., "Catalytic action of L-methionine γ-lyase on selenomethionine and selenols," Biochemistry, vol. 18(3), 1979, pp. 407-410.*
G. Scambia et al.; *"Growth Inhibitory Effect of Diheptyl Diselenide on Various Human Cancer Cell Lines"*; Anticancer Research vol. 9, pp. 1967-1700 (1989).

* cited by examiner

*Primary Examiner*—John Pak
(74) *Attorney, Agent, or Firm*—Christie, Parker & Hale, LLP

(57) ABSTRACT

Compositions are provided for the topical treatment of cancer consisting of lotions, creams, sprays, suppositories or slow-release transdermal patches containing lipid-soluble, skin-penetrating organic selenium compounds in combination with inert carriers in therapeutically effective amounts of selenium compound. The selenium compounds are medium linear chain dialkyl diselenides and precursors such as alkyl selenols. Preferred compositions employ R—Se—Se—R compounds where R is from 6 to 8 carbon atoms, and most specifically di-n-hexyl diselenide. Commonly used carriers may be purified hydrocarbon fractions, oils, with or without added fat-soluble vitamins, water and emulsifying agents.

3 Claims, No Drawings

COMPOSITIONS FOR THE TREATMENT AND PREVENTION OF CANCER

CROSS REFERENCE TO RELATED APPLICATIONS

This divisional patent application claims the benefit of non-provisional U.S. application Ser. No. 10/179,712, filed Jun. 24, 2002, now U.S. Pat. No. 6,867,238 which claims the benefit of provisional U.S. Application Ser. No. 60/300,408, filed Jun. 22, 2001.

BACKGROUND

Selenium is an essential trace element and is the functional component of several important enzymes and which is increasingly also recognized for its anticarcinogenic properties. The glutathione peroxidases, for example, prevent the build-up of hydrogen peroxide and lipid hydroperoxides and thus help to protect cells and tissues from damage by reactive oxygen species. Since oxygen radicals attacking DNA may cause mutations resulting in the transformation of normal cells into cancer cells, selenium by virtue of its antioxidant properties can counteract these processes thereby acting as a cancer-protecting agent.

Selenium in addition to its anti-mutagenic properties may alter carcinogen metabolism and prevent DNA methylation and other mechanisms believed to play a role in carcinogenesis. Selenium is also required for the maintenance of the functions of the immune system. At pharmacological levels, selenium is known to exert cytotoxic effects on tumor cells without adversely affecting normal cells. For example, sodium selenite added to the growth media caused the selective destruction of human hepatoma and lung cancer cells without affecting normal embryonic liver or lung cells; see: S. Y. Yu, et al, Biol. Trace El. Res. 15: 243-255 (1987); A. Pung et al., Biol. Trace El. Res. 14: 29-42 (1987). Selenium compounds accordingly are receiving attention as potential cancer therapeutic agents. Selenium preparations for a variety of therapeutic uses are already available, most of which are for oral administration or by injection.

A number of selenium-containing preparations for topical applications have also been claimed. For example, in U.S. Pat. No. 4,865,840, the use of lotions or creams containing selenomethionine was claimed for the prevention of ultraviolet radiation-induced skin damage. In U.S. Pat. No. 4,512,977, selenium compounds are claimed for the topical treatment of damage caused by surgical incisions, lacerations and burns. The compounds claimed in these patents are water soluble.

A lipid soluble organo selenium compound, di-n-hexyl diselenide, has previously been used in cancer therapy, but only in preparations for oral or parenteral administration (E. Revici, Research in Physiopathology as Basis of Guided Chemotherapy, Van Nostrand Company, New York, 1961, pp.512-518). The related compound di-n-diheptyl diselenide, was shown to inhibit the growth of several human cancer cell lines in cell cultures [see G. Scambia et al., Anticancer Res. 9: 1697-1700, (1989). In German Patent 43 20694.8-41, preparations containing dialkyl diselenides were claimed for the topical treatment of warts. For cancer treatment, preparations containing dialkyl diselenides and related compounds have previously been claimed only for oral or parenteral administration. For example, in DE-3408362 C2, dialkyl diselenides of the general composition R—Se—Se—R, with R being an alkyl or alkenyl group with an odd number of carbon atoms in combination with an aliphatic ketone were claimed as oral and parenteral drugs for the treatment of cancer. In EP-0095663, the reaction product of selenium with eleostearic acid was claimed as an anti-neoplastic drug for oral or parenteral administration.

SUMMARY OF THE INVENTION

In the present invention there are provided formulations of lipid soluble organic selenium compounds for topical application in humans and animals. The topical selenium preparations may be used for the prevention or treatment of cancer in organs such as the skin, the breast, the rectum, and the large intestine. Effective compounds are dialkyl diselenides of general composition R—Se—Se—R, wherein R denotes a linear or branched alkyl residue with 6 to 8 carbon atoms. The length of the alkyl chain R significantly affects the physical properties of these compounds, notably their volatility and skin-penetrating ability. Dialkyl diselenides of composition R—Se—Se—R with organic residues R containing 6 carbon atoms such as di-n-hexyl diselenide, $C_6H_{13}$—Se—Se—$C_6H_{13}$, are preferred for topical applications because these compounds penetrate the skin most effectively. Dialkyl diselenides with fewer than 6 carbon atoms attached to the —Se—Se— moiety are too volatile for topical applications.

Passage of the dialkyl diselenides through the skin is facilitated by transporting agents as carriers in the composition. Successful transporting agents comprise aliphatic hydrocarbons including but not limited to n-decane, n-undecane and n-dodecane, whereby the prefix n- denotes that the carbon chain is linear and unbranched. Branched hydrocarbons and other carriers that tend to plug pores and thereby impede transfer through skin are generally undesirable. The carrier preferably comprises an aliphatic hydrocarbon with 10 to 12 carbon atoms.

The dialkyl diselenides may also be added to vegetable oils such as safflower oil, sunflower oil, sesame oil, avocado oil, jojoba oil, wheat germ oil, olive oil, and fragrant oils; they can also be dissolved in cacao butter or in polyethylene glycol when they are to be used in suppositories.

Depending on their intended use, the concentration of the selenium compounds in the different compositions may range from 0.01 to 40%. The preferred concentration ranges upon application of the composition onto skin are in the range of from 0.1% to 20%. The concentration in a spray composition where some of the carrier evaporates upon application to skin may be as low as 0.01%.

Cancerous lesions are typically treated by direct application of the dialkyl diselenide containing lotion. Adhesive patches impregnated with the lotions can be used, allowing the selenium compounds to be slowly released into the tumor. The selenium compounds may also be applied in the form of creams or sprays. These may contain from 0.01 to 20% by weight of the selenium compounds. Creams may contain the commonly used base materials, including but not limited to sesame oil, safflower oil, wheat germ oil, stearic acid, cetyl alcohol, glycerol, triethanol amine, retinyl palmitate, allantoin, methyl paraben, imidazolidinyl urea, fragrant oils and water. Sprays contain the selenium compounds in an inert solvent such as n-decane, or light petrolatum and a propellant such as compressed air, nitrogen, carbon dioxide or the like.

DETAILED DESCRIPTION

I have found that certain preparations of dialkyl diselenides in appropriate solvents or dispersion media can be used for the topical treatment and prevention of cancer from precancerous conditions. Dialkyl diselenides are preferred embodiments in the present invention because of their low systemic toxicity and their lipophilic characteristics. The external application of select dialkyl diselenides in combination with appropriate transporting agents allows the temporary build-up of locally high concentrations of the selenium compounds in, or in the immediate vicinity of tumors. Absorbed selenium is not accumulated in the body. It disperses from the site of administration and is normally eliminated in due course.

The therapeutic efficacy of the dialkyl diselenides of these compositions depends on (1) the length of the alkyl residue R, and (2) the composition of the inert carrier as these determine the degree to which they can penetrate through the skin. For example, a lotion containing di-n-hexyl diselenide in n-decane shows excellent skin penetration properties. Increasing the average alkyl chain length beyond n-hexyl causes them to become less skin penetrating and more suitable for the treatment of superficial cancerous lesions. Shortening the chain length below n-hexyl increases the volatility of these compounds. This reduces their therapeutic efficacy as it causes them to evaporate when brought onto the skin.

The dialkyl diselenides may also be applied in the form of lotions, creams, or sprays. These preparations may contain additional ingredients, namely fats or oils of plant, animal or synthetic origin, emulsified fat- or water-soluble vitamins, mineral oils, hormones, prohormones, antihormones, antineoplastic drugs, fragrances and analgesic substances, organ extracts, plant extracts, synthetic or natural polymeric substances, along with water and emulsifiers.

The dialkyl diselenides may also be applied in the form of suppositories into body cavities, using low-melting natural or synthetic lipophilic substances such as cocoa butter or polyethylene oxide, polyethylene glycol or polypropylene glycol as inert carriers. The selenium compounds may also be dissolved in suitable polymeric carriers to allow them to be applied in the form of adhesive tapes or transdermal patches for the slow release the selenium compounds through skin. Lotions, creams or patches containing dialkyl diselenides may be applied onto entire organs suspected to harbor tumor cells. For example, such compositions may be periodically applied onto the breast, resulting in the temporary build-up of locally high concentrations of these organo selenium compounds, providing a novel means of breast cancer prevention.

According to current knowledge, cancer cells develop from normal cells in a stepwise process involving several mutations and other irreversible genetic changes. The process may be triggered by a wide variety of agents and stress factors, including high-energy radiation, viruses, chronic irritants, toxic heavy metals, certain chemicals and drugs. Cells after one mutational event may still be essentially benign but may subsequently undergo further changes and become malignant. Malignant cells are usually recognized as foreign by the cells of the immune system and are destroyed. However, cells evading the immunological surveillance system will continue to proliferate and accumulate, initially forming a small, avascular tumor. This tumor will grow slowly until it develops its own blood supply, at which point growth rates usually increase, and sometimes dramatically.

The present invention provides compositions for cancer treatment and prevention that can be applied in the earliest as well as in more advanced stages of tumor development. The compositions consist of combinations of members of a group of relatively nontoxic lipid soluble organic selenium compounds with inert carriers to facilitate their transport through the skin. Treatment of a tumor is accomplished by applying these compositions directly onto the tumor or on the skin above and around it. The organo-selenium compounds may be applied in the form of lotions, creams, sprays or suppositories (via mucous tissues similar to dermal tissue). In addition, they may be dissolved in polymeric matrices to be used as transdermal patches for their slow release into affected areas.

The organo selenium compounds may also rubbed on in the form of creams or oils onto the skin. In this manner, locally high concentrations of the organo selenium species can be generated in organs at risk of developing cancer. The active ingredients in the compositions for external cancer treatment are select medium-chain dialkyl diselenides, R Se Se R, in combination with suitable inert carriers.

Selection of the appropriate alkyl residues R in these compounds is important as it determines their ability to penetrate the skin. Preferred are dialkyl diselenides with linear, medium-length straight alkyl residues of at least 6 and not exceeding 8 carbon atoms. The reason for this limitation of the alkyl chain length is that the di-n-alkyl diselenides with fewer than 6 carbon alkyl chains are too volatile, while those with alkyl chains exceeding 8 carbon atoms fail to significantly penetrate the skin.

The alkyl residues on the diselinide need not be equal. Thus, for example, two carbon chain lengths of 5 and 7 carbon atoms, respectively, on a diselenide are considered equivalent to di-n-hexyl diselenide. Other equivalencies having suitable volatility and skin absorption properties will be apparent.

The dialkyl diselenides may be applied in inert or physiologically acceptable carriers such as n-decane, or light petrolatum, for example. When they are to be applied in rubbing oils for preventive rather than therapeutic purposes, base materials in common usage such as sesame oil, safflower oil, wheat germ oil, squalane, stearic acid, cetyl alcohol, glycerol, triethanol amine, retinyl palmitate, allantoin, methyl paraben, imidazolidinyl urea, and fragrant oils may be used. These ingredients along with emulsifying agents and water are typically used in creams containing the organic selenium compounds. Other ingredients include DL-a-tocopherol (vitamin E), DL-a-tocopheryl acetate (vitamin E acetate) or vitamin A. Other materials on the GRAS list, or now or hereafter having regulatory approval for application to skin are equivalent. For use in suppositories the selenium compounds are dissolved in cacao butter, polyethylene glycol or similar low-melting polymers such as polypropylene glycol melting at about 37° C.

Other materials now or hereafter having regulatory approval for suppositories are equivalent.

When applied in the form of sprays, solutions of the selenium compounds in physiologically acceptable inert carriers and a propellant such as compressed air, nitrogen, CO2 or the like may be used. The present invention thus comprises compositions containing these dialkyl diselenides and related organo selenium compounds along with carriers such as solvents or dispersion agents for topical use in the treatment and prevention of cancer. The organo selenium compounds are dialkyl diselenides of composition R—Se—Se—R, where R is an alkyl residue. Precursors of diselenides such as the alkyl selenols, R—SeH are equivalent since these compounds are readily converted to dialkyl diselenides by reaction with oxygen. A drawback to the selenols is unpleasant odor.

Compositions suitable for topical treatment and prevention of cutaneous and subcutaneous cancer and pre-cancerous conditions are solutions or dispersions of one or more lipophilic dialkyl diselenides in a physiologically acceptable carrier capable of absorption through skin. The diselenide can be stated as R—Se—Se—R and R is preferably in the range of from 6 to 8 carbon atoms. Broadly stated, the proportion of dialkyl diselenide is therapeutically effective. Specifically the proportion is in the range of from 0.1 to 40% and preferably up to 20%. A specific range is found to be 6 to 12% in an aliphatic hydrocarbon or from 1 to 10% in oils. A particularly preferred dialkyl diselenide comprises di-n-hexyl diselenide. Good carriers include liquid aliphatic hydrocarbons, particularly those with from 10 to 12 carbon atoms. An example of an excellent carrier is n-decane. Other carriers include sesame oil, safflower oil, wheat germ oil, squalane, stearic acid, cetyl alcohol, glycerol, triethanol amine, retinyl palmitate, allantoin, methyl paraben, imidazolidinyl urea, fragrant plant oils, DL-a-tocopherol, DL-a-tocopheryl acetate, vitamin A, and light petrolatum, and commonly used base materials as equivalents. The carrier may effectively be inert or may contain other therapeutic agents compatible with the diselenide. When used as a suppository a suitable composition has from 0.1 to 10% dialkyl diselenide in cocoa butter, polypropylene glycol, polyethylene glycol or other materials having a melting point of about 37° C. and having regulatory approval for suppositories. When used in a spray, the concentration of diselenide may be proportionately diminished by the presence of propellants.

When used in a transdermal patch for slow release in the topical treatment of cutaneous and subcutaneous cancerous and precancerous conditions the organo-selenium compound is dispersed in a plastic substrate with or without additional carriers.

As pointed out above, precursors of the dialkyl diselenides are equivalent. For example, the composition may contain an alkyl selenol of composition R—SeH, with the chain length of the alkyl group R ranging from 6 to 8 carbon atoms (or, for example, from 5 to 9 where the R residues of the dialkyl diselenide are not equal). A preferred precursor is n-hexylselenol. A suitable composition is, for example, from 6 to 12% dissolved in n-decane.

Details of the invention and certain preferred embodiments thereof will be further understood upon reference to the following examples. Percentages are by volume unless otherwise indicated.

EXAMPLE I

A male subject of age 65 years presented with a skin lesion of 0.8 cm diameter on his right upper chest. The lesion had doubled in size during the past two months and displayed all characteristics of a superficially spreading melanoma. Topical application of a 10% solution of di-n-dihexyl diselenide in n-decane, twice a day for 3 days, caused a layer of dead cells to be formed which dropped off after 4 days without leaving a scar.

EXAMPLE II

A male subject aged 66 years presented with a small irregular melanotic spot of approximately 3 mm diameter on his right hand which the subject had since birth but which in recent years had increased in size and became unsymmetrical. Topical application of a 10% solution of di-n-hexyl diselenide in a 1:1 (volume per volume) mixture of n-decane and n-dodecane once every day for one week caused the affected skin to turn brittle and to fall off. New skin growing over the lesion closed it without a scar.

EXAMPLE III

A 70 year old male diagnosed with a squamous carcinoma on his nose applied a cream containing 6% di-n-heptyl diselenide in a base of safflower oil, stearic acid, cetyl alcohol, glyceryl stearate, DL-a-tocopherol, fragrant plant oils and purified water, onto the affected area twice per day for 5 days resulting in the disappearance of the lesion.

EXAMPLE IV

A woman aged 63 developed a lesion diagnosed as precancerous on the upper part of her back. Application of an adhesive bandage impregnated with di-n-octyl diselenide caused the lesion to dry out and drop off without a scar within 3 weeks.

EXAMPLE V

A woman aged 38 years with a small lump on her breast was told that she was at risk of developing breast cancer. She applied onto her breasts once a week a cream containing 0.2% di-n-hexyl diselenide in a moisturizing cream of conventional composition. The lump in her breast disappeared over a period of two months. She presently continues to apply the selenium composition once a week as a precautionary measure.

EXAMPLE VI

In May 1998 a tumor was diagnosed in the left breast of a woman which had been treated for cancer of the right breast in 1974 by mastectomy, axillar resection, chemotherapy with cytoxan, metothrexate and 5-fluorouracil, and ovariectomy. In May 1999 she presented with numerous skin metastases on her upper torso and lymph node involvement. The patient underwent various therapies in Europe, which included chemotherapy, immunotherapy and hyperthermia, but numerous metastatic cutaneous and subcutaneous metastatic lesions remained on her chest, in the mastectomy scar, in the left axilla and on her back. The topical application of 5% di-n-hexyl diselenide in n-decane onto these lesions and the affected lymph nodes caused their disappearance within two weeks. She remained free of cancer for two years after which recurrences on her chest and metastases on her back reappeared. These were effectively controlled by the topical application of a 10% solution of n-hexyl selenol in n-decane. She has remained free of obvious signs of cancer for one year. As a precaution she is applying a lotion containing 0.2% solution of di-n-hexyl diselenide in jojoba oil onto areas of her skin once every two weeks.

EXAMPLE VII

A woman aged 48 years was diagnosed in July 1999 with a high nuclear grade intraductal carcinoma of the right breast. The tumor consisted of a hard mass in the lower left quadrant of the right breast of 3 cm diameter. In November 1999, a 6% di n-hexyl diselenide in a 1:1 mixture of n-decane and jojoba oil was applied onto the affected breast once per day. Over a period of 4 weeks the breast mass shrunk and ultimately disappeared. Status Jan. 8, 2000: No breast mass detectable by ultrasonic examination. Status April 2001: Unchanged.

EXAMPLE VIII

A woman aged 62 was diagnosed with inoperable cancer of the rectum in 1998 and was offered radiation therapy, which she refused. A colostomy was performed in the fall of 1998.

She applied suppositories containing 2% di-n-hexyl diselenide in cocoa butter daily into her rectum for a period of 4 weeks. During the following 2 years, her status has remained stable, she gained weight, and was able to work. X-ray and sonographic examinations demonstrated that the tumor mass had ceased to grow.

Whereas, in the above examples, certain preferred proportions of the components of the compositions are given, these may be varied, where suitable, with similar results. Other variations of the topical applications will occur to those skilled in the art upon reading this disclosure. Those are intended to be included within the scope of this invention as defined in the appended claims and equivalents thereof.

The invention claimed is:

1. An article of manufacture comprising:
a transdermal patch for topical treatment of cutaneous and subcutaneous cancer and precancerous conditions, said patch containing organoselenium compound therein, said compound comprising an alkyl selenol, the alkyl radical of which is in the range of from 5 to 9 carbon atoms.

2. The article of manufacture of claim 1, wherein the alkyl radical is in the range of from 6 to 8 carbon atoms.

3. The article of manufacture as recited in claim 1, wherein the organoselenium compound is n-hexyl selenol.

* * * * *